United States Patent [19]

Krämer et al.

[11] 4,283,406
[45] Aug. 11, 1981

[54] COMBATING BOTRYTIS FUNGI WITH 1-(2,4-DICHLOROPHENYL)-1-(2,6-DIHALOGENOBENZYLOXIMINO)-2-(1,2,4-TRIAZOL-1-YL)-ETHANES

[75] Inventors: Wolfgang Krämer; Hans-Joachim Knops; Karl H. Büchel, all of Wuppertal; Wilhelm Brandes, Leichlingen, all of Fed. Rep. of Germany

[73] Assignee: Bayer Aktiengesellschaft, Leverkusen, Fed. Rep. of Germany

[21] Appl. No.: 141,834

[22] Filed: Apr. 21, 1980

[30] Foreign Application Priority Data

May 8, 1979 [DE] Fed. Rep. of Germany ....... 2918467

[51] Int. Cl.³ .................... A01N 43/64; C07D 249/08
[52] U.S. Cl. .................... 424/269; 548/262; 564/256
[58] Field of Search .................... 424/269; 548/262

[56] References Cited

U.S. PATENT DOCUMENTS

| 4,086,351 | 4/1978 | Balasubramanyan et al. | 548/262 |
| 4,113,465 | 9/1978 | Shephard et al. | 548/341 |

FOREIGN PATENT DOCUMENTS

2723942 12/1978 Fed. Rep. of Germany ........... 548/262

Primary Examiner—Alton D. Rollins
Attorney, Agent, or Firm—Sprung, Felfe, Horn, Lynch & Kramer

[57] ABSTRACT

A method of combating Botrytis fungi, comprising applying to such fungi, or to a habitat thereof to be protected against such fungus a fungicidally effective amount of a 1-(2,4-dichlorophenyl)-1-(2,6-dihalogenobenzyloximino)-2-(1,2,4-triazol-1-yl)-ethane of the formula

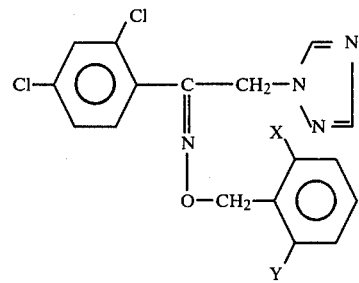

in which
X and Y each independently is halogen or a physiologically acceptable acid addition salt thereof. Those compounds in which X is chlorine or fluorine and Y is fluorine are new.

7 Claims, No Drawings

COMBATING BOTRYTIS FUNGI WITH 1-(2,4-DICHLOROPHENYL)-1-(2,6-DIHALOGENOBENZYLOXIMINO)-2-(1,2,4-TRIAZOL-1-YL)-ETHANES

The present invention relates to the use of 1-(2,4-dichlorophenyl)-1-(2,6-dihalogenobenzyloximino)-2-(1,2,4-triazol-1-yl)-ethanes, some of which are known, as selective fungicides against Botrytis fungi.

It has already been disclosed that 1-(2,4-dichlorophenyl)-1-(halogenobenzyloximino)-2-(1,2,4-triazol-1-yl)-ethanes have a very good fungicidal activity (see DE-OS (German Published Specification) No. 2,723,942). However, nothing was hitherto known of their activity against Botrytis fungi, which is of high interest from an economic point of view.

It has been found that, specifically, 1-(2,4-dichlorophenyl)-1-(2,6-dihalogenobenzyloximino)-2-(1,2,4-triazol-1-yl)-ethanes of the general formula

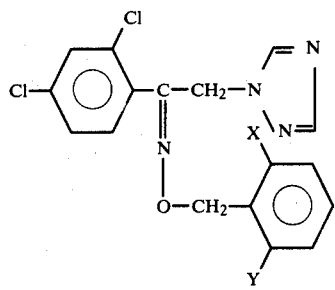

in which
X and Y are identical or different and represent halogen, and
physiologically acceptable acid addition salts thereof have a particularly good selective fungicidal activity against Botrytis fungi.

Accordingly, the invention provides a method of combating Botrytis fungi which comprises applying to the fungi, or to a habitat thereof, a compound of the formula (I) or a physiologically acceptable acid addition salt thereof, alone or in admixture with a diluent or carrier.

The compounds of the formula (I) can exist in the syn-form or anti-form; they are predominantly obtained as mixtures of the two forms.

Surprisingly, the 1-(2,4-dichlorophenyl)-1-(2,6-dihalogenobenzyloximino)-2-(1,2,4-triazol-1-yl)-ethanes of the formula (I) exhibit a considerably more powerful selective fungicidal action than the comparable 1-(2,4-dichlorophenyl)-1-(halogenobenzyloximino)-2-(1,2,4-triazol-1-yl)-ethanes known from the state of the art, for example the corresponding 2,4-dichlorobenzyloximino, 4-chlorobenzyloximino and 2-chlorobenzyloximino derivatives, which are very closely related compounds from a chemical point of view.

The new use of the active compounds thus represents an enrichment of the art.

Formula (I) provides a definition of the compounds which can be used according to the invention. Preferably, in this formula, X represents chlorine or fluorine and Y represent chlorine or fluorine. Some of the compounds are known (see DE-OS (German Published Specification) No. 2,723,942). Those compounds of the formula (I) in which X and Y do not simultaneously represent chlorine have not been disclosed hitherto in the literature. Those substances of the formula (I) in which X denotes chlorine or fluorine while Y is always fluorine are thus interesting new compounds.

The compounds of the formula (I) can be obtained in a known manner, if, in a first stage, ω-halogeno-2,4-dichloroacetophenones are reacted with 1,2,4-triazole in the presence of an inert organic solvent and in the presence of an acid-binding agent, at temperatures between 20° and 120° C.; the ω-(1,2,4-triazol-1-yl)-2,4-dichloroacetophenones formed are reacted, in a second stage, with hydroxylamine in the presence of a solvent, preferably an alcohol, at 50° to 100° C., the hydroxylamine preferably being employed as the hydrochloride in the presence of an acid-binding agent; and, in a third stage, the ω-(1,2,4-triazol-1-yl)-2,4-dichloroacetophenone oximes formed are reacted with 2,6-dihalogenobenzyl halides in the presence of an inert organic solvent and if appropriate in the presence of a strong base, at temperatures between 20° and 100° C. (in this context, see also the statements in DE-OS (German Published Specification) No. 2,657,578 and DE-OS (German Published Specification) No. 2,723,942).

The compounds of the formula (I) can also be obtained by a new process which does not belong to the state of the art (see U.S. application Ser. No. 120168, filed Feb. 11, 1980 by reacting ω-halogeno-dichloroacetophenones of the general formula

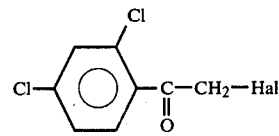

in which
Hal represents halogen, preferably chlorine or bromine,
with hydroxylamines of the general formula

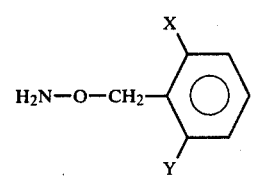

in which
X and Y have the meanings indicated above, in the presence of a diluent, preferably an alcohol or aqueous alcohol, at temperatures between 50° and 100° C., the hydroxylamines of the formula (III) preferably being employed in the form of their hydrochlorides in the presence of an acid-binding agent; and reacting the ω-halogeno-2,4-dichloroacetophenone oxime ethers thereby formed of the general formula

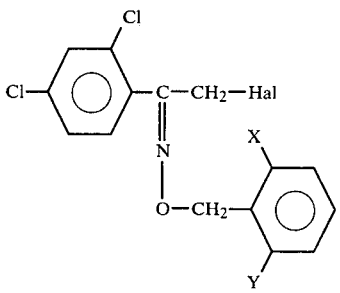

in which

X, Y and Hal have the meanings indicated above, with 1,2,4-triazole in the presence of an organic solvent and in the presence of an acid-binding agent, for example potassium carbonate, at temperatures between 60° and 120° C. In a particular embodiment, this process can also be carried out as a so-called one-pot process, without isolation of the intermediate products of the formula (IV) and without changing the solvent (see also the preparative examples given later in this text).

Any of the physiologically acceptable acids can be used for the preparation of acid addition salts of the compounds of the formula (I). These acids include, as preferences, hydrogen halide acids (for example hydrobromic acid and in particular hydrochloric acid), phosphoric acid, nitric acid, sulphuric acid, monofunctional and bifunctional carboxylic acids and hydroxycarboxylic acids (for example acetic acid, maleic acid, succinic acid, fumaric acid, tartaric acid, citric acid, salicyclic acid, sorbic acid and lactic acid) and sulphonic acids (for example p-toluenesulphonic acid and 1,5-naphthalenedisulphonic acid).

The salts of the compounds of the formula (I) can be obtained in a simple manner by customary salt formation methods, for example by dissolving a compound of the formula (I) in a suitable inert solvent and adding the acid, for example hydrochloric acid, and they can be isolated in a known manner, for example by filtration, and if appropriate purified by washing with an inert organic solvent.

The active compounds of the formula (I) exhibit a powerful microbicidal action and can be employed in practice for combating undesired micro-organisms. The active compounds are suitable for use as plant protection agents.

Fungicidal agents in plant protection are employed for combating Plasmodiophoromycetes, Oomycetes, Chytridiomycetes, Zygomycetes, Ascomycetes, Basidiomycetes and Deuteromycetes.

The good toleration, by plants of the active compounds, at the concentrations required for combating plant diseases, permits treatment of above-ground parts of plants, of vegetative propagation stock and seeds, and of the soil.

The active compounds of the formula (I) display a particularly good activity against Botrytis fungi, for example against Botrytis cinerea, the causative organism of grey mold in beans, lettuce, strawberries and vines.

The active compounds can be converted into the customary formulations, such as solutions, emulsions, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention can be present in the formulations, or in the various use forms, as a mixture with other active compounds, such as fungicides, bactericides, insecticides, acaricides, nematicides, herbicides, bird repellents, growth factors, plant nutrients and agents for improving soil structure.

The active compounds can be used as such, as their formulations or as the use forms prepared therefrom by further dilution, such as ready-to-use solutions, emulsions, suspensions, powders, pastes and granules. They may be used in the customary manner, for example by watering, immersion, spraying, atomizing, misting, vaporizing, injecting, brushing on, dusting, scattering, dry dressing, moist dressing, wet dressing, slurry dressing or encrusting.

Especially in the treatment of parts of plants, the active compound concentrations in the use forms can be varied within a substantial range. They are, in general, from 1 to 0.0001% by weight, preferably from 0.5 to 0.001%.

In the treatment of seed, amounts of active compound of in general 0.001 to 50 g, preferably 0.01 to 10 g, are employed per kilogram of seed.

For the treatment of soil, active compound concentrations of in general 0.00001 to 0.1% by weight, preferably 0.0001 to 0.02%, are employed at the place of action.

The invention also provides crops protected from damage by Botrytis fungi by being grown in areas in which immediately prior to and/or during the time of the growing a compound of the formula (I) or a physiologically acceptable acid-addition salt thereof was applied, alone or in admixture with a diluent or carrier.

It will be seen that the usual methods of providing a harvested crop may be improved by the present invention.

PREPARATIVE EXAMPLES

Example 1

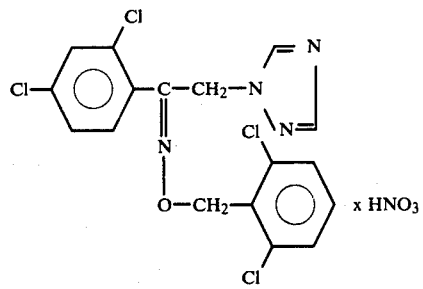

27.1 g (0.1 mol) of ω-(1,2,4-triazol-1-yl)-2,4-dichloroacetophenone oxime were suspended in 300 ml of toluene, and 300 ml of 45% strength sodium hydroxide solution and then 3 ml of benzyl-dimethylammonium chloride were added. 43 g (about 0.22 mol) of 2,6-dichlorobenzyl chloride were added dropwise, while stirring, and the mixture was stirred at 40° C. for 10 hours. The phases were separated, the organic phase was washed twice with 300 ml of saturated sodium chloride solution each time and dried over sodium sulphate and the solvent was distilled off under a water-pump vacuum. The residue was taken up in 100 ml of chloroform, and 3 ml of concentrated nitric acid were added dropwise, while cooling with ice. The product was allowed to crystallize out and the precipitate was filtered off and rinsed twice with 50 ml of diethyl ether. 23 g (42% of theory) of ω-(1,2,4-triazol-1-yl)-2,4-dichloroacetophenone oxime 2,6-dichlorobenzyl ether nitrate of melting point 160° C. (decomposition) were obtained.

Example 2

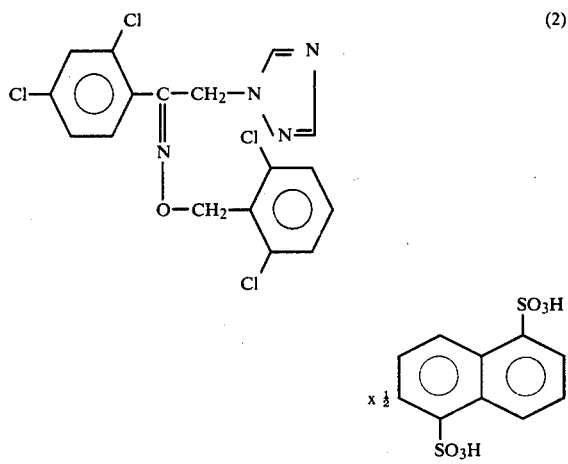

8.9 g (0.04 mol) of ω-chloro-2,4-dichloroacetophenone, 8.6 g (0.04 mol) of O-2,6-dichlorobenzylhydroxylamine hydrochloride and 3.3 g (0.04 mol) of sodium acetate in 100 ml of ethanol were heated under reflux for 15 hours. 2.8 g (0.04 mol) of 1,2,4-triazole and 5.6 g (0.04 mol) of potassium carbonate were added to this reaction mixture and the mixture was heated under reflux for a further 20 hours. After cooling, the mixture was filtered and the filtrate was concentrated. The residue was taken up in 250 ml of methylene chloride, washed five times with 200 ml of water each time, dried over sodium sulphate and concentrated. 15.4 g (89.5% of theory) of ω-(1,2,4-triazol-1-yl)-2,4-dichloroacetophenone oxime O-2,6-dichlorobenzyl ether were obtained as an oil. To form the salt, this oil was dissolved in acetone. A solution of 5.4 g of 1,5-naphthalenedisulphonic acid in 25 ml of acetone was filtered in, the mixture was stirred at room temperature for 10 minutes and the precipitate was filtered off. 14.8 g (72% of theory, relative to base employed) of ω-(1,2,4-triazol-1-yl)-2,4-dichloroacetophenone oxime 2,6-dichlorobenzyl ether-1,5-naphthalenedisulphonate of melting point 245°-252° C. (decomposition) were obtained.

The following compounds of the general formula

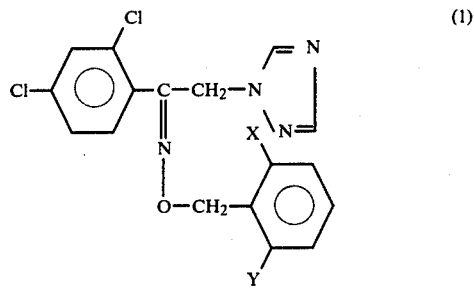

could be obtained in a corresponding manner:

TABLE 1

| Compound No. | X | Y | Melting point (°C.) |
|---|---|---|---|
| 3 | Cl | F | 135 (decomposition)(xHNO₃) |

TABLE 1-continued

| Compound No. | X | Y | Melting point (°C.) |
|---|---|---|---|
| 4 | F | F | oil |
| 5 | Cl | F | 50-70 |

The anti-Botrytis activity of the compounds of this invention is illustrated by the following example wherein the compounds according to the present invention are each identified by the number (given in brackets) from Examples 1 and 2 hereinabove:

Example 3

Botrytis test (lettuce)/protective
Solvent: 4.7 parts by weight of acetone
Dispersing agent: 0.3 part by weight of alkylaryl polyglycol ether
Water: 95.00 parts by weight The amount of active compound required to give the desired concentration of active compound in the spray liquid was mixed with the stated amount of the solvent, and the concentrate was diluted with the stated amount of water which contained the stated additive.

Lettuce plants in the 8-leaf stage were sprayed with the spray liquid until dripping wet. After 24 hours, 2 small pieces of agar covered with *Botrytis cinerea* were placed on each leaf. The inoculated plants were placed in a darkened, moist chamber at 20° C. 3 days after the inoculation, the size of the infected spots on the leaves was rated.

The ratings were converted to percent infection. 0% denoted no infection and 100% meant that the plants were completely infected.

The active compounds, the concentrations of the active compounds and the results can be seen from the following table:

TABLE 2

Botrytis-test (lettuce)/protective

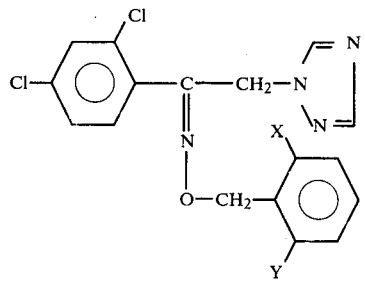

It will be appreciated that the instant specification and examples are set forth by way of illustration and not limitation, and that various modifications and changes may be made without departing from the spirit and scope of the present invention.

We claim:

1. A method of combating Botrytis fungi, comprising applying to such fungi, or to a habitat thereof to be protected against such fungus, a fungicidally effective amount of a 1-(2,4-dichlorophenyl)-1-(2,6-dihalogenobenzyloximino)-2-(1,2,4-triazol-1-yl)-ethane of the formula in which
X and Y each independently is chlorine or fluorine or a physiologically acceptable acid addition salt thereof.

2. The method according to claim 1, in which X and Y each is chlorine.

3. The method according to claim 1, in which X and Y each is fluorine.

4. The method according to claim 1, in which X is chlorine and Y is fluorine.

5. The method according to claim 1, in which the active compound is applied to soil in an amount of about 0.00001 to 0.1 percent by weight.

6. The method according to claim 1, in which the active compound is applied to seed in an amount of about 0.001 to 50 g per kg of seed.

7. The method according to claim 1, in which the active compound is applied to a growing crop.

* * * * *